United States Patent

Canady

[11] Patent Number: 5,207,675
[45] Date of Patent: May 4, 1993

[54] SURGICAL COAGULATION DEVICE
[76] Inventor: Jerome Canady, 4000 16th St., N.W., Washington, D.C. 20011
[21] Appl. No.: 730,049
[22] Filed: Jul. 15, 1991
[51] Int. Cl.$^5$ .................................. A61B 17/36
[52] U.S. Cl. ........................................ 606/40; 606/37; 606/46; 606/49
[58] Field of Search ............... 606/32, 33, 34, 39, 606/40, 41, 45, 46, 49, 50, 51, 52

[56] References Cited

U.S. PATENT DOCUMENTS

| | | | |
|---|---|---|---|
| 2,011,169 | 8/1935 | Wappler | 606/49 X |
| 3,858,586 | 1/1975 | Lessen | 606/49 |
| 4,040,426 | 8/1977 | Morrison, Jr. | 606/49 |
| 4,618,885 | 10/1986 | Nagasaki et al. | 606/46 X |
| 4,708,137 | 11/1987 | Tsukagoshi | 606/46 |
| 4,901,719 | 2/1990 | Trenconsky et al. | 606/49 |
| 4,943,290 | 7/1990 | Rexroth et al. | 606/49 |
| 5,041,110 | 8/1991 | Fleenor | 606/37 X |

OTHER PUBLICATIONS

Ward et al., "A Significant New Contribution to Radical Head and Neck Surgery", *Archives of Otolaryngology-Head Neck Surg.*, 115:921-923 (1989).
Hernandez et al., "A Controlled Study of the Argon Beam Coagulator for Partial Nephrectomy", *The Journal of Urology*, 143:1062-1065 (1990).
Brand et al., "Electrosurgical Debulking of Ovarian Cancer: A New Technique Using the Argon Beam Coagulator", *Gyencologic Oncology*, 39:115-118 (1990).

*Primary Examiner*—Peter A. Aschenbrenner
*Attorney, Agent, or Firm*—Rothwell, Figg, Ernst & Kurz

[57] ABSTRACT

A surgical tissue coagulator includes an elongate, biocompatible, flexible tube having an open distal end and a proximal end. The tube has an external diameter of less than about 5 mm, and is insertable into and maneuverable within a surgical endoscope. The proximal end of the tube is connectable with a source of argon gas so that a stream of the gas can flow through the tube and exit the distal end of the tube. A flexible wire is provided within the tube for conducting radiofrequency (RF) current. The wire has a distal end for positioning adjacent the distal end of the tube, and a tungsten tip is provided at the distal end of the wire for discharging an arc of RF energy away from the distal end of the wire within the stream of argon gas exiting the distal end of the tube. The wire has a proximal end opposite the distal end thereof. The wire is connectable at the proximal end thereof with a source of RF energy. A handle is attached to the tube adjacent the proximal end of the tube for maneuvering the tube within the endoscope while the handle is outside the endoscope. The process of the invention utilizes the surgical tissue coagulator defined above.

16 Claims, 2 Drawing Sheets

SURGICAL COAGULATION DEVICE

BACKGROUND OF THE INVENTION

1. Field of the Invention

The present invention relates to the field of surgical coagulation of tissue.

2. Description of the Background Art

Controlling or arresting blood loss is of high priority during surgery so as to avoid or minimize the necessity of introducing foreign blood or blood products into a patient. This has increased in importance due to concern over contamination of the blood supply by viral agents which cause, for example, acquired immune deficiency syndrome (AIDS), hepatitis, and the like.

Presently, the standard means for controlling traumatic and surgical blood loss are electrosurgical generators and lasers, which respectively direct high-frequency electrical currents or light energy to localize heat in bleeding vessels so as to coagulate the overlying blood and vessel walls.

Recently, argon beam coagulators have been demonstrated to be effective tissue coagulators. Presently available argon beam coagulators include a flexible cable having a nozzle tip with an opening through which argon gas flows. The device includes a handle immediately adjacent the nozzle tip for placing the tip in position for tissue coagulation. Within the tip is located a tungsten needle for discharging radiofrequency (RF) current which ionizes the argon gas. The stream of ionized argon, a colorless, odorless, inactive gas, conducts the current to the tissue and blood vessels, while effectively blowing blood away from the vessels and allowing coagulation within vessel walls.

Argon beam coagulator systems have been utilized to control or arrest blood flow in various types of incisional surgeries, including radical head and neck surgery, Ward, et al., *Archives of Autolaryngology-Head and Neck Surgery.* 115:921-923 (1989): and partial nephrectomy, Hernandez, et al., *The Journal of Urology,* 143:1062-1065 (1990). The argon beam coagulator system has also been utilized for electrosurgical debulking of ovarian cancer, Brand, et al., *Gynecologic Oncology,* 39:115-118 (1990). However, the configuration of currently available argon beam coagulators has prevented their use in other forms of surgery.

There is a need in the art for an argon beam coagulator which can be utilized in surgical applications which are not presently available.

SUMMARY OF THE INVENTION

In accordance with the present invention, a surgical tissue coagulator comprises an elongate, biocompatible, flexible tube having an open distal end and a proximal end. The tube has an external diameter of less than about 5 mm, and is insertable into and maneuverable within a surgical endoscope. Means are provided for connecting the proximal end of the tube with a source of an inert, ionizable gas, so that a stream of the gas can flow through the tube and exit the distal end of the tube. A flexible wire is provided within the tube for conducting radiofrequency (RF) current. The wire has a distal end for positioning adjacent the distal end of the tube, and means at the distal end of the wire for discharging an arc of RF energy away from the distal end of the wire within the stream of inert gas exiting the distal end of the tube. The wire has a proximal end opposite the distal end of the wire, and means for connecting the proximal end of the wire with a source of RF energy. A handle is attached to the adjacent proximal end of the tube, for maneuvering the tube within the endoscope while the handle is outside the endoscope. The process of the invention comprises placing a surgical endoscope in the vicinity of tissue to be coagulated, and inserting a surgical tissue coagulator, as defined above, into the surgical endoscope. The distal end of the surgical tissue coagulator is positioned in the proximity of tissue to be coagulated. A stream of inert, ionizable gas is passed from the distal end of the coagulator while discharging RF energy therefrom, so as to coagulate the tissue.

DETAILED DESCRIPTION OF THE PREFERRED EMBODIMENTS

Figure 1:
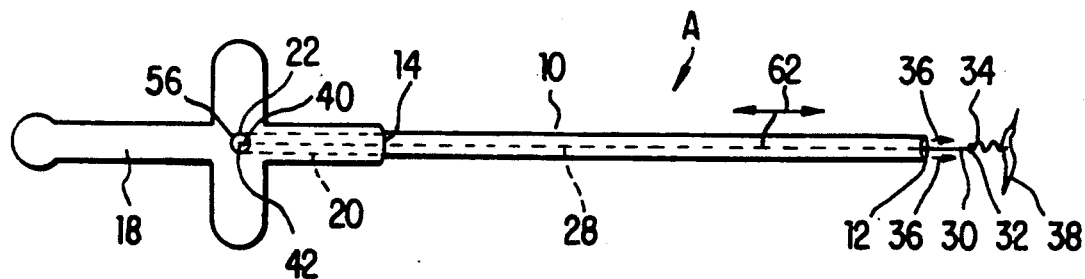
FIG. 1 is a partly schematic, elevational view of a surgical tissue coagulator in accordance with one embodiment of the present invention.
Figure 2:
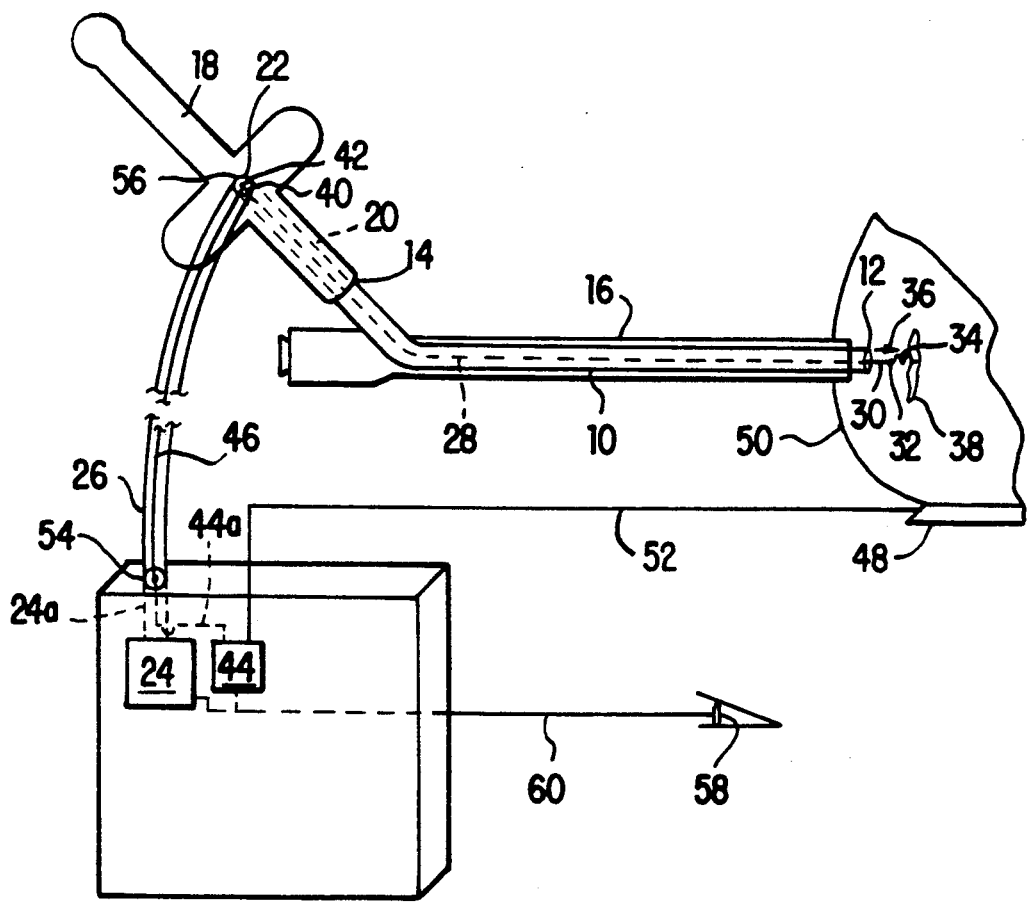
FIG. 2 is a partly schematic, plan view of a surgical tissue coagulator in accordance with one embodiment, attached to a base unit and inserted within a surgical endoscope for tissue coagulation in a patient.

With reference to FIGS. 1 and 2, a surgical tissue coagulator A in accordance with the present invention includes an elongate, biocompatable, flexible tube 10 having an open distal end 12 and a proximal end 14. Tube 10 can be formed of any suitable biocompatible, flexible material, and in preferred embodiments, is formed of polymeric material. In particularly preferred embodiments, tube 10 is SILASTIC ® tubing (Dow).

Tube 10 has an external diameter of less than about 5 mm, and is insertable into, and maneuverable within, a surgical endoscope 16 (shown in FIG. 2). The present invention is usable with any suitable endoscope, such as those manufactured by Olympus, Pentax and Fujinon. Typical endoscopes, such as Hystereoscopes, gastroscopes, colonoscopes and laparoscopes, have a length within the range of from about 35 cm to about 120 cm.

Endoscopes with which the present invention is usable have working channels through which surgical instruments can be inserted into the patient. Such working channels have diameters of about 3.8 mm to about 4 mm. A coagulator in accordance with the present invention must have a tube 10 with an outer diameter less than the internal diameter of the working channel of an endoscope through which tube 10 is inserted. Accordingly, with endoscopes having working channels of from about 3.8 mm to about 4 mm, coagulators in accordance with the present invention have a flexible tube 10 with an outer diameter of about 3-3.5 mm. In particularly preferred embodiments, tube 10 has an external diameter of about 3 mm.

Referring back to FIG. 1, a handle 18 is attached to tube 10 adjacent the proximal end 14 of the tube. Handle 18 is provided for maneuvering tube 10 within endoscope 16 (shown in FIG. 2) while handle 18 is outside the endoscope.

As shown in FIG. 1, end 14 of tube 10 is connected to a passageway 20 in handle 18 which in turn is connected to connector means 22 for connecting the proximal end 14 of tube 10 with a source of an inert, ionizable gas, such as argon. Connection with the source of gas provides for a stream of inert gas to flow through tube 10 and exit distal end 12 of the tube.

A flexible wire 28 is provided within tube 10 for conducting radiofrequency (RF) current. In preferred embodiments, wire 10 has an external diameter of about 1 mm.

Wire 28 has a distal end 30 for positioning adjacent the distal end 12 of tube 10. Means 32 are provided at the distal end 30 of wire 28 for discharging an arc 34 of RF energy away from the distal end of wire 28, within the stream of inert gas (represented by arrows 36 exiting the distal end 12 of tube 10.)

In preferred embodiments, the RF discharging means at the end 30 of wire 28 comprises a tungsten tip 32. In accordance with one embodiment, tungsten tip 32 is at least partly spherical. In the embodiment shown in FIG. 1, tungsten tip 32 comprises a tungsten ball.

The inert, ionizable argon gas provides the medium through which the arc 34 travels to the surface of tissue 38 so as to coagulate tissue 38.

Wire 28 has a proximal end 40 and connector means 42 for connecting the proximal end of the wire with a source of RF energy.

The surgical tissue coagulator A of the present invention can easily be configured for use with commercially available argon gas coagulator base units, such as the base unit for the Bard System 6000 ™ electrosurgical generator with argon beam coagulation (ABC) shown schematically in FIG. 2 with reference letter B (Bard Electromedical Systems, Inc., Englewood Colorado).

Base unit B includes a source of argon gas 24 and a source of RF energy in the form of RF generator 44.

Base unit B includes a coaxial outlet 54 with a gas source 24 and RF generator 44. Outlet 54 is the coaxial terminus of gas line 24a connected with gas source 24, and RF line 44a connected with RF generator 44.

Handle 18 of coagulator A includes a coaxial inlet 56 which includes gas connector means 22, within which is coaxially located RF connector means 42.

The coaxial inlet 56 of coagulator A is connectable with the coaxial outlet 54 of base unit B by means of gas line 26, within which is located RF line 46. Thus, gas line 26 connects gas inlet 42 of coagulator A with argon source 24 of base unit B via line 24a, while RF line 46 connects RF inlet 42 of coagulator A with RF generator 44 of base unit B via line 44a.

Any suitable connector means can be utilized to connect the ends of line 26 with coaxial outlet 54 and coaxial inlet 56, such as threaded connectors, leur lock connectors, and the like. Also, any suitable electrical connector can be utilized to connect line 46 with line 44a of base unit B and RF inlet 42 of coagulator A.

A ground plate 48 in contact with patient 50 is provided for return of RF current to generator 44 via line 52.

Base unit B is activated by a single pedal foot switch 58 connected to base unit B via line 60. Activation of switch 58 opens argon source 24 and activates generator 44.

Argon gas can be provided by source 24 with a variable gas flow rate of, for example, from 1 to 12 liters/minute.

RF generator 44 can deliver, for example, from 40 to 150 W radiofrequency current. RF current flows when tip 30 of wire 28 comes within about 1 cm of tissue 38, while foot pedal switch 58 is depressed. The arcing current in the gas jet ionizes the argon gas. The inert, noncombustible argon gas provides the medium through which the argon travels.

FIG. 2 shows an endoscope 16 within patient 50 in the vicinity of tissue 38 to be coagulated. Tube 10 of coagulator A has been inserted within endoscope 16 in the proximity of tissue 38, i.e., within about 1 cm thereof.

With foot pedal switch 58 depressed, a stream of argon gas exits distal end 12 of tube 10 while RF energy is discharged from tip 30 of wire 28 into tissue 38.

Referring back to FIG. 1, wire 28 is longitudinally movable within tube 10 in directions shown by double-ended arrow 62 so that the distal end 30 and tip 32 of wire 28 is movable from a position within tube 10 to the position shown outside the distal end of tube 10. Control of the movement of wire 28 within tube 10 can be by any suitable means, such as under the control of flexible handle 18.

Figure 3:
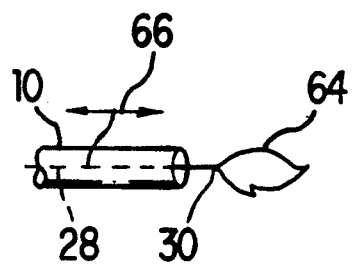
FIG. 3 is a partly schematic, detailed view of the tip of a surgical tissue coagulator in accordance with one embodiment of the invention, having a polypectomy snare as an additional feature.

If desired, additional surgical instruments can be provided at the distal end 30 of wire 28. For example, in the embodiment shown in FIG. 3, a polypectomy snare 64 is attached to the distal end 30 of wire 28. In the embodiment shown, polypectomy snare 64 is movable with wire 28 from inside tube 10 to outside tube 10, in the directions shown by double-ended arrow 66. In accordance with this embodiment, polyps can be captured with snare 64 and tissue can be cauterized by RF energy passing from the distal end 30 of wire 28.

Figure 4:
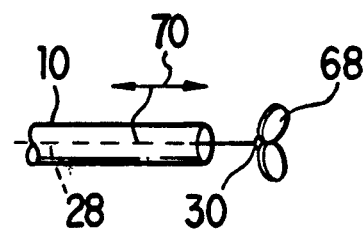
FIG. 4 is a partly schematic, detailed view showing the tip of a surgical tissue coagulator in accordance with another embodiment of the invention, having biopsy forceps as an additional feature.
Figure 5:
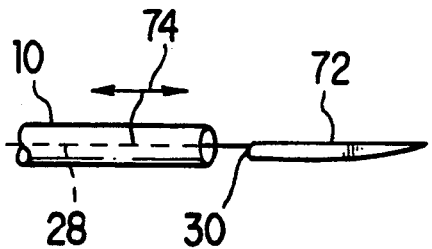
FIG. 5 is a partly schematic, detailed view of a surgical tissue coagulator tip according to another embodiment of the present invention, having a dissection needle as an additional feature.

In another embodiment, biopsy forceps 68 for grasping tissue are attached to the distal end 30 of wire 28 as shown in FIG. 4. In accordance with this embodiment, forceps 68 are movable from inside tube 10 to outside tube 10, along with wire 28, in the directions shown by double-ended arrow 70. In accordance with this embodiment, RF current can be delivered from end 30 of wire 28. The biopsy forceps can be advanced out of tubing 10 and the biopsy forceps can grasp tissue. The biopsy forceps can also be pulled back into tubing 10.

In yet another embodiment, the RF discharging means at the end 30 of wire 28 further comprises a titanium dissection needle 72 for dissecting tissue. The dissecting needle 72 is movable with the end 30 of wire 28 from inside tube 10 to outside tube 10 in the directions shown by double-ended arrow 74. In accordance with this embodiment, titanium needle 72 can be advanced out of tubing 10 and the titanium needle can be utilized to discharge RF current within the argon gas stream so as to coagulate tissue. Subsequently, tissue can be dissected from its origin of attachment using needle 72.

Since many modifications, variations and changes in detail may be made to the described embodiments, it is intended that all matter in the foregoing description and shown in the accompanying drawings be interpreted as illustrative and not in a limiting sense.

What is claimed is:

1. A surgical tissue coagulator comprising an elongate, biocampatible, flexible tube having an open distal end and a proximal end, the tube having an external diameter of less than about 5 mm and being insertable into and maneuverable within a surgical endoscope;

means for connecting the proximal end of said tube with a source of an inert, ionizable gas so that a stream of said gas can flow through said tube and exit the distal end of said tube;

a flexible wire within said tube for conducting radiofrequency current, the wire having a distal end for positioning adjacent the distal end of said tube, and means at the distal end of said wire fir discharging an arc of radiofrequency energy away from the distal end of said wire within said stream of inert gas exiting the distal end of said tube so as to form an ionized gas stream which is capable of coagulating tissue during endoscopic surgery within a patient, the wire having a proximal end opposite the distal end of the wire, and means for connecting the proximal end of the wire with a source of radiofrequency energy; and a handle attached to said tube adjacent the proximal end of the tube for maneuvering said tube within said endoscope while said handle is outside said endoscope 2. The surgical tissue coagulator of claim 1 wherein said wire is longitudinally movable within said tube.

3. The surgical tissue coagulator of claim 2 wherein the distal end of said wire is movable from a position within said tube to a position outside the distal end of said tube.

4. The surgical tissue coagulator of claim 3 further including a polypectomy snare attached to the distal end of said wire, which snare is movable from inside said tube to outside said tube.

5. The surgical tissue coagulator of claim 3 further including biopsy forceps for grasping tissue, said forceps being attached to the distal end of said wire, said forceps being movable from inside said tube to outside said tube.

6. The surgical tissue coagulator of claim 3 wherein the discharging means further comprises a titanium dissection needle for dissecting tissue, said needle being movable from inside said tube to outside said tube.

7. The surgical tissue coagulator of claim 1 wherein said wire has an external diameter of about 1 mm.

8. The surgical tissue coagulator of claim 1 wherein the discharging means at the distal end of said wire comprises a tungsten tip.

9. The surgical tissue coagulator of claim 8 wherein said tungsten tip is at least partly spherical.

10. The spherical tissue coagulator of claim 9 wherein said tip comprises a tungsten ball.

11. The surgical tissue coagulator of claim 1 wherein said means for connecting the proximal end of said tube with a source of inert gas comprises a means for connecting the proximal end of said tube with a source of argon gas so that a stream of said argon gas can flow through said tube and exit the distal end of said tube.

12. The surgical tissue coagulator of claim 1 wherein said endoscope is selected from the group consisting of gastroscope, Hysteroscope, colonoscope and laparoscope.

13. A process for coagulating tissue during endoscopic surgery, comprising undertaking endoscopic surgery by:

a) placing a surgical endoscope in the vicinity of a patient's tissue to be coagulated;

b) inserting a surgical tissue coagulator into the patient through a working channel of said endoscope, said surgical tissue coagulator comprising an elongate, biocompatible, flexible tube having an open distal end and a proximal end, the tube having an external diameter of less than about 5 mm and being insertable into and maneuverable within a surgical endoscope;

means for connecting the proximal end of said tube with a source of an inert, ionizable gas so that a stream of said gas can flow through said tube and exit the distal end of said tube;

a flexible wire within said tube for conducting radiofrequency current, the wire having a distal end for positioning adjacent the distal end of said tube, and means at the distal end of said wire for discharging an arc of radiofrequency energy away from the distal end of said wire within said stream of inner gas exiting the distal end of said tube, the wire having a proximal end opposite the distal end of the wire, and means for connecting the proximal end of the wire with a source of radiofrequency energy; and a handle attached to said tube adjacent the proximal end of the tube for maneuvering said tube within said endoscope while said handle is outside said endoscope;

c) positioning the distal end of said tube within said patient in the proximity of tissue to be coagulated;

d) passing a stream of inert, ionizable gas out the distal end of said tube while discharging radiofrequency energy from the tip of said wire so as to form an ionized gas stream and coagulate said tissue with said ionized gas stream.

14. The process of claim 13 wherein said passing step comprises passing a stream of argon gas.

15. The surgical tissue coagulator of claim 1 in combination with a surgical endoscope.

16. The surgical tissue coagulator of claim 15 wherein said endoscope is selected from the group consisting of gastroscope, hysteroscope, colonoscope and laparoscope.

* * * * *

US005207675C1

(12) REEXAMINATION CERTIFICATE (4773rd)

United States Patent
Canady

(10) Number: US 5,207,675 C1
(45) Certificate Issued: Apr. 22, 2003

(54) SURGICAL COAGULATION DEVICE

(75) Inventor: Jerome Canady, 4000 16th St., NW., Washington, DC (US) 20011

(73) Assignee: Jerome Canady, Washington, DC (US)

Reexamination Request:
No. 90/005,757, Jun. 21, 2000
No. 90/006,115, Sep. 24, 2001
No. 90/006,128, Oct. 12, 2001

Reexamination Certificate for:
Patent No.: 5,207,675
Issued: May 4, 1993
Appl. No.: 07/730,049
Filed: Jul. 15, 1991

(51) Int. Cl.$^7$ ............................................. A61B 18/18
(52) U.S. Cl. ............................ 606/40; 606/46; 606/49; 606/37
(58) Field of Search ............................ 606/40, 41, 45, 606/46, 49, 50

(56) References Cited

U.S. PATENT DOCUMENTS

| | | | | |
|---|---|---|---|---|
| 4,781,175 A | * | 11/1988 | McGreevy et al. | 606/40 |
| 4,943,290 A | * | 7/1990 | Rexroth et al. | 119/51.02 |
| 5,041,110 A | * | 8/1991 | Fleenor | 606/34 |
| 5,122,138 A | * | 6/1992 | Manwaring | 606/46 |
| 5,720,745 A | * | 2/1998 | Farin et al. | 606/49 |

FOREIGN PATENT DOCUMENTS

DE                3508784 A1    *   9/1986

OTHER PUBLICATIONS

Papp, John P, "Endoscopic Control of Gastrointestinal Hemorrhage", Chapter 3, pp31–42, 1981.*
Daniell et al., "Laparoscopic Evaluation of the Argon Beam Coagulator" Journal of Reproductive Medicine, vol. 38, No. 2, pp. 121–125, Feb. 1993.*
Daniell et al., "Laparascopic Treatment of Endometriosis With the Argon Beam Coagulator", Gynecological Endoscopy, vol. 2, pp. 13–19, 1993.*
Matthews, "Argon Beam Coagulation", AORN Journal, vol. 56, No. 5, Nov. 1992.*
Floyd, "Magic Wand Stops Surgical Bleeding", The Tennessean, vol. 87, No. 40, May 1991.*
Daniell et al "Abstract: Early Investigations of the Argon Beam Coagulator for Laparoscopic Control of Intra–Abdominal Bleeding", Presentation for the American Fertility Society, Oct. 1991.*
Farello et al, "Laparoscopic Cholecystectomy Using Argon Bistoury", 13: (4), pp163–164, Apr. 1992.*
Lange et al, "Minimally Invasive Interventions in Solitary Liver Cysts", 63(4), pp 349–352, Apr. 1992.*
Reed, "Clinical Report No. 9: Argon Beam Coagulator for Liver Bed Bleeding During Laparoscopic Cholecystectomy", 1991.*

* cited by examiner

*Primary Examiner*—Michael Peffley

(57) ABSTRACT

A surgical tissue coagulator includes an elongate, biocompatible, flexible tube having an open distal end and a proximal end. The tube has an external diameter of less than about 5 mm, and is insertable into and maneuverable within a surgical endoscope. The proximal end of the tube is connectable with a source of argon gas so that a stream of the gas can flow through the tube and exit the distal end of the tube. A flexible wire is provided within the tube for conducting radiofrequency (RF) current. The wire has a distal end for positioning adjacent the distal end of the tube, and a tungsten tip is provided at the distal end of the wire for discharging an arc of RF energy away from the distal end of the wire within the stream of argon gas exiting the distal end of the tube. The wire has a proximal end opposite the distal end thereof. The wire is connectable at the proximal end thereof with a source of RF energy. A handle is attached to the tube adjacent the proximal end of the tube for maneuvering the tube within the endoscope while the handle is outside the endoscope. The process of the invention utilizes the surgical tissue coagulator defined above.

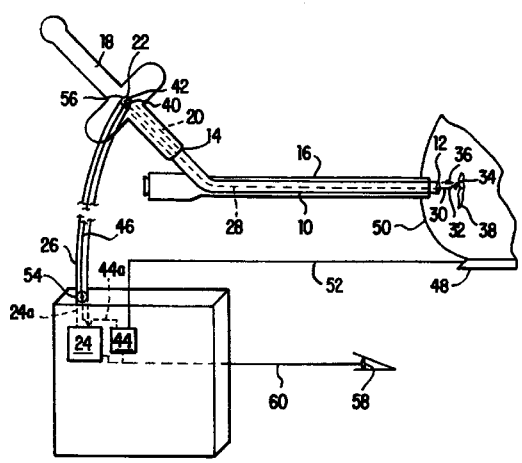

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–16 is confirmed.

* * * * *